United States Patent [19]

Förster et al.

[11] Patent Number: 4,988,380
[45] Date of Patent: Jan. 29, 1991

[54] USE OF DIFLUOROMETHYL-THIADIAZOLYL-OXYACETAMIDES AS SELECTIVE HERBICIDES

[75] Inventors: Heinz Förster, Wuppertal; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 366,579

[22] Filed: Jun. 15, 1989

[30] Foreign Application Priority Data

Jun. 27, 1988 [DE] Fed. Rep. of Germany ....... 3821597

[51] Int. Cl.$^5$ .................... C07D 285/12; A01N 43/82
[52] U.S. Cl. .......................................... 71/90; 548/136
[58] Field of Search ............................ 548/136; 71/90

[56] References Cited

U.S. PATENT DOCUMENTS 4,005,213  1/1977  Nüsslein et al. .................. 71/90
4,509,971  4/1985  Forster et al. .................... 71/90
4,708,731  11/1987 Forster ............................. 71/90

FOREIGN PATENT DOCUMENTS 0148501  7/1985  European Pat. Off. ............. 71/90
0298338  1/1989  European Pat. Off. ............. 71/90

Primary Examiner—Robert Gerstl
Attorney, Agent, or Firm—Sprung Horn Kramer & Woods

[57] ABSTRACT

A process for selectively combating weeds in crops, comprising applying to a locus in which such crops are growing or are to be grown a herbicidally effective amount of a difluoromethyl-thiadiazolyl-oxy-acetamide of the formula

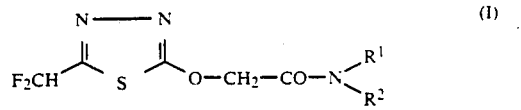

in which
$R^1$ stands for hydrogen or for an optionally substituted radical from the group consisting of alkyl, alkenyl, alkinyl and aralkyl,
$R^2$ stands for an optionally substituted radical from the group consisting of alkyl, alkenyl, alkinyl, cycloalkyl, cycloalkenyl, aralkyl, aryl, alkoxy, alkenyloxy and alkinyloxy, or
$R^1$ and $R^2$ together with the nitrogen atom to which they are bonded form an optionally substituted, saturated or unsaturated heterocycle which can contain further hetero atoms and to which a benzo group may be fused.

Compounds wherein $R^1$ is $C_2$-$C_4$-alkyl and $R^2$ is optionally substituted phenyl are new as are intermediates of the formula

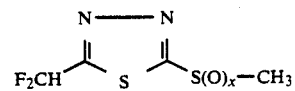

in which x is 0 or 2.

9 Claims, No Drawings

USE OF DIFLUOROMETHYL-THIADIAZOLYL-OXYACETAMIDES AS SELECTIVE HERBICIDES

The invention relates to the use of difluoromethyl-thiadiazolyl-oxyacetamides, some of which are known, as selective herbicides for various crops, furthermore to a group of novel difluoromethyl-thiadiazolyl-oxyacetamides and to a process and novel intermediates for their preparation.

It has already been disclosed that certain heteroaryloxyacetamides, such as, for example, N-methyl-2-(benzothiazol-2-yl-oxy)-acetanilide, exhibit herbicidal properties (cf. EP-A 5,501 and U.S. Pat. No. 4,509,971). However, the herbicidal activity of the previously known compounds is not always completely satisfactory.

Furthermore, certain difluoromethyl-thiadiazolyloxyacetamides have been described (cf. EP-A-148,501 and U.S. Pat. No. 4,708,731). However, nothing has been known to date about the actual herbicidal properties of these compounds, in particular about any selective-herbicidal properties which might be present.

It has now been found that the difluoromethyl-thiadiazolyl-oxyacetamides, some of which are known, of the general formula (I)

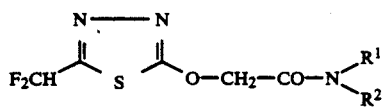

in which
R$^1$ stands for hydrogen or for an optionally substituted radical from the series comprising alkyl, alkenyl, alkinyl or aralkyl,
R$^2$ stands for an optionally substituted radical from the series comprising alkyl, alkenyl, alkinyl, cycloalkyl, cycloalkenyl, aralkyl, aryl, alkoxy, alkenyloxy or alkinyloxy, or
R$^1$ and R$^2$ together with the nitrogen atom to which they are bonded form an optionally substituted, saturated or unsaturated heterocycle which can contain further hetero atoms and to which a benzo group may be fused,
exhibit powerful herbicidal action while having good selectivity in useful plants.

Surprisingly, the difluoromethyl-thiadiazolyloxyacetamides of the general formula (I) show a considerably more powerful herbicidal action against common weeds which are difficult to combat than the above-mentioned compounds, while being well tolerated by important crop plants.

The invention preferably relates to the use of herbicides and to herbicides based on compounds of the general formula (I) in which
R$^1$ stands for hydrogen, C$_1$-C$_8$-alkyl which is optionally substituted by fluorine, chlorine, cyano or C$_1$-C$_4$-alkoxy, for C$_2$-C$_8$-alkenyl which is optionally substituted by fluorine and/or chlorine, for C$_2$-C$_8$-alkinyl or for benzyl,
R$^2$ stands for C$_1$-C$_8$-alkyl which is optionally substituted by fluorine, chlorine, cyano or C$_1$-C$_4$-alkoxy, for C$_2$-C$_8$-alkenyl which is optionally substituted by fluorine and/or chlorine, for C$_2$-C$_8$-alkinyl, for C$_3$-C$_6$-cycloalkyl which is optionally substituted by chlorine and/or C$_1$-C$_3$-alkyl, for C$_5$- or C$_6$-cycloalkenyl, for benzyl which is optionally substituted by fluorine, chlorine and/or C$_1$-C$_4$-alkyl, for phenyl which is optionally substituted by fluorine, chlorine, bromine, iodine, cyano, nitro, C$_1$-C$_4$-alkyl, trifluoromethyl, C$_1$-C$_4$-alkoxy and/or C$_1$-C$_4$-alkylthio, for C$_1$-C$_8$-alkoxy which is optionally substituted by C$_1$-C$_4$-alkoxy, or for C$_3$-C$_4$alkenyloxy, or
R$_1$ and R$_2$ together with the nitrogen atom to which they are bonded form a saturated or unsaturated, five- to seven-membered nitrogen heterocycle which is optionally monosubstituted to trisubstituted by C$_1$-C$_3$-alkyl and which is optionally benzo-fused and which can contain an oxygen atom as a further hetero atom.

Compounds of the formula (I) which are particularly preferably used according to the invention are those in which
R$_1$ stands for C$_1$-C$_4$-alkyl, allyl or propargyl,
R$_2$ stands for C$_1$-C$_6$-alkyl, C$_1$-C$_2$-alkoxy-C$_1$-C$_2$-alkyl, allyl, propargyl, cyclopentyl, cyclohexyl, cyclohexenyl, benzyl, phenyl (which is optionally substituted by fluorine, chlorine, bromine, cyano, nitro, methyl, ethyl, trifluoromethyl, methoxy, ethoxy), C$_1$-C$_6$-alkoxy or C$_1$-C$_2$-alkoxy-C$_1$-C$_2$-alkoxy, or
R$^1$ and R$^2$ together with the nitrogen atom to which they are bonded stand for piperidinyl which is optionally monosubstituted to trisubstituted by methyl and/or ethyl, for pyrrolidinyl which is optionally monosubstituted or disubstituted by methyl and/or ethyl, for perhydroazepinyl or for 1,2,3,4-tetrahydroquinolinyl.

Examples of the compounds of the formula (I) to be used according to the invention are listed in Table 1 below.

TABLE 1

Examples of the compounds of the formula (I)

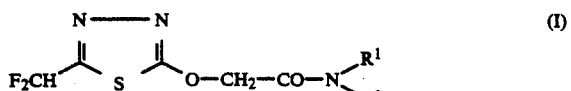

| Example No. | R$^1$ | or $-N{<}^{R^1}_{R^2}$ R$^2$ | Physical data |
|---|---|---|---|
| 1 | CH$_3$ | 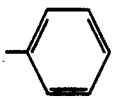 | Melting Point: 67° C. |

TABLE 1-continued

Examples of the compounds of the formula (I)

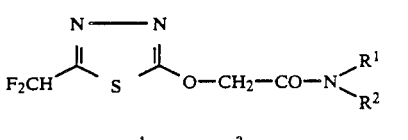

| Example No. | $R^1$ or $-N\binom{R^1}{R^2}$ | $R^2$ | Physical data |
|---|---|---|---|
| 2 | CH(CH$_3$)$_2$ |  | Melting point: 98° C. |
| 3 | CH(CH$_3$)$_2$ | 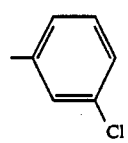 | Melting point: 69° C. |
| 4 | CH(CH$_3$)$_2$ |  | Melting point: 113° C. |
| 5 | CH(CH$_3$)$_2$ | 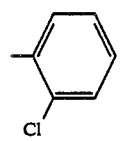 | Melting point: 123° C. |
| 6 | CH$_3$ | 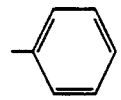 | Melting point: 47° C. |
| 7 | CH(CH$_3$)$_2$ | OCH$_2$CH$_2$OC$_2$H$_5$ | $n_D^{20}$: 1.4679 |
| 8 | CH$_3$ | 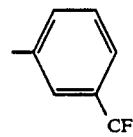 | Melting point: 83° C. |
| 9 | 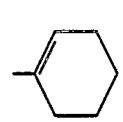 | | Melting point: 73° C. |
| 10 | CH$_3$ | C$_4$H$_9$ | $n_D^{20}$: 1.4827 |
| 11 | 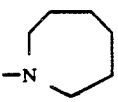 | | $n_D^{20}$: 1.5385 |
| 12 | C$_2$H$_5$ | C$_2$H$_5$ | $n_D^{20}$: 1.4857 |
| 13 | C$_2$H$_5$ | 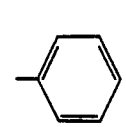 | Melting point: 70° C. |

TABLE 1-continued

Examples of the compounds of the formula (I)

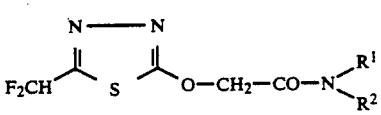

(I)

| Example No. | R¹ | R² or $-N\langle_{R^2}^{R^1}$ | | Physical data |
|---|---|---|---|---|
| 14 | | ![1,2,3,4-tetrahydroquinolin-1-yl] | | $n_D^{20}$: 1.5500 |
| 15 | CH₃ | ![4-nitro-2-methylphenyl] | | Melting point: 188° C. |
| 16 | | ![3-methylpiperidin-1-yl] | | $n_D^{20}$: 1.4998 |
| 17 | CH₃ | ![2,3-dimethylphenyl] | | Melting point: 132° C. |
| 18 | | ![2-ethylpiperidin-1-yl] | | Melting point: 81° C. |
| 19 | C₃H₇ | C₃H₇ | | $n_D^{20}$: 1.4787 |
| 20 | CH₂CH=CH₂ | CH₂CH=CH₂ | | Melting point: 64° C. |
| 21 | CH₃ | CH₂C≡CH | | $n_D^{20}$: 1.4968 |
| 22 | CH₃ | ![2,6-dimethylphenyl] | | Melting point: 112° C. |
| 23 | CHC₂H₅<br>\|<br>CH₃ | OCH₃ | | Melting point: 55° C. |
| 24 | CHC₂H₅<br>\|<br>CH₃ | CH₂OCH₃ | | |
| 25 | C₄H₉ | C₄H₉ | | $n_D^{20}$: 1.4775 |

TABLE 1-continued

Examples of the compounds of the formula (I)

$$F_2CH-C(=N-N=)-S-C(=)-O-CH_2-CO-NR^1R^2 \quad (I)$$

| Example No. | $R^1$ | $R^2$ or $-NR^1R^2$ | Physical data |
|---|---|---|---|
| 26 | CH₃ | –⟨C₆H₄⟩–Cl (4-Cl) | Melting point: 97° C. |
| 27 | | –N(piperidinyl) | |
| 28 | | –N(4-methylpiperidinyl) | |
| 29 | CH(CH₃)₂ | –⟨C₆H₄⟩–F (2-F) | Melting point: 128° C. |
| 30 | CH(CH₃)₂ | –⟨C₆H₄⟩–F (3-F) | Melting point: 120° C. |
| 31 | CH(CH₃)₂ | –⟨C₆H₄⟩–F (4-F) | Melting point: 97° C. |
| 32 | CH(CH₃)₂ | –⟨C₆H₄⟩–CH₃ (3-CH₃) | Melting point: 95° C. |
| 33 | CH(CH₃)₂ | –⟨C₆H₄⟩–CH₃ (4-CH₃) | |
| 34 | CH₃ | –⟨C₆H₄⟩–Cl (3-Cl) | Melting point: 83° C. |
| 35 | CH₃ | –⟨C₆H₄⟩–CH₃ (3-CH₃) | Melting point: 102° C. |

TABLE 1-continued

Examples of the compounds of the formula (I)

$$F_2CH-C(=N-N=)-S-C(=)-O-CH_2-CO-N(R^1)(R^2) \quad (I)$$

| Example No. | R$^1$ | R$^2$ or $-N(R^1)(R^2)$ | Physical data |
|---|---|---|---|
| 36 | CH$_3$ | 4-CH$_3$-C$_6$H$_4$- | |
| 37 | CH$_3$ | 2-Cl-C$_6$H$_4$- | |
| 38 | CH(CH$_3$)$_2$ | 3-CF$_3$-C$_6$H$_4$- | |
| 39 | CH$_3$ | 4-OCH$_3$-C$_6$H$_4$- | |
| 40 | CH(CH$_3$)$_2$ | 4-OCH$_3$-C$_6$H$_4$- | Melting point: 66° C. |
| 41 | CH$_3$ | 2-F-C$_6$H$_4$- | |
| 42 | CH$_3$ | 3-F-C$_6$H$_4$- | |
| 43 | CH$_3$ | 4-F-C$_6$H$_4$- | |
| 44 | C$_2$H$_5$ | 4-F-C$_6$H$_4$- | |
| 45 | | 3,5-dimethylpiperidin-1-yl | Melting point: 63° C. |

TABLE 1-continued

Examples of the compounds of the formula (I)

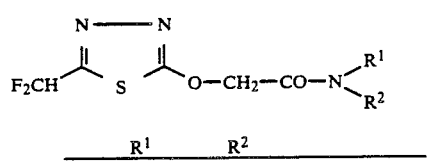

(I)

| Example No. | R$^1$    R$^2$  or $-N{<}^{R^1}_{R^2}$ | Physical data |
|---|---|---|
| 46 | -N(piperidine with 3-C$_2$H$_5$) | n$_D^{20}$: 1.5005 |
| 47 | -N(piperidine with 2-CH$_3$, 4-CH$_3$) | Melting point: 54° C. |
| 48 | CH$_3$    CH$_2$OCH$_3$ | n$_D^{20}$: 1.4772 |
| 49 | CH—CHCH$_2$CH$_3$   OCH$_3$<br>\|    \|<br>CH$_3$  CH$_3$ | n$_D^{20}$: 1.4715 |
| 50 | CH$_3$    CH$_3$ | Melting point: 69° C. |
| 51 | C$_2$H$_5$    (3-methylphenyl) | Melting point: 75° C. |
| 52 | -N(morpholine) | Melting point: 112° C. |
| 53 | C$_2$H$_5$    CH$_2$CF$_3$ | Melting point: 59° C. |
| 54 | CH$_2$CH(CH$_3$)$_2$    (phenyl) | Melting point: 93° C. |
| 55 | -N(1,2,3,6-tetrahydropyridine) | n$_D^{20}$: 1.5070 |
| 56 | C$_2$H$_5$    C$_4$H$_9$ | n$_D^{20}$: 1.4769 |
| 57 | CH(CH$_3$)$_2$    (2-methoxyphenyl) | Melting point: 72° C. |
| 58 | CH(CH$_3$)$_2$    (4-ethoxyphenyl) | Melting point: 34° C. |

TABLE 1-continued

Examples of the compounds of the formula (I)

| Example No. | R$^1$ | R$^2$ or —N(R$^1$)(R$^2$) | Physical data |
|---|---|---|---|
| 59 | CH(CH$_3$)$_2$ | 3,4-dichlorophenyl | Melting point: 64° C. |
| 60 | CH(CH$_3$)$_2$ | 3-chloro-4-(methylthio)phenyl | Melting point: 125° C. |
| 61 | CH(CH$_3$)$_2$ | 2,5-bis(trifluoromethyl)phenyl | Melting point: 103° C. |
| 62 | CH(CH$_3$)$_2$ | 2,5-dimethylphenyl | Melting point: 95° C. |
| 63 | CH(CH$_3$)$_2$ | 2,5-dichlorophenyl | Melting point: 111° C. |
| 64 | CH(CH$_3$)$_2$ | 3-chloro-4-methoxyphenyl | Melting point: 150° C. |
| 65 | CH(CH$_3$)$_2$ | 4-chloro-3-methylphenyl | Melting point: 88° C. |
| 66 | CH$_3$ | 4-methylphenyl | Melting point: 107° C. |

The compounds of the formula (I) have been disclosed and/or can be prepared by processes known per se (cf. U.S. Pat. No. 4,708,731).

Some of the compounds of the formula (I) were hitherto unknown. The present invention thus also relates to novel difluoromethylthiadiazolyl-oxyacetamides of the general formula (Ia)

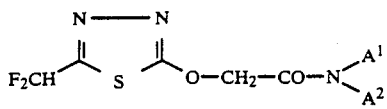

in which
A¹ stands for $C_2$–$C_4$-alkyl and
A² stands for optionally substituted aryl.

The novel difluoromethyl-thiadiazolyl-oxyacetamides of the general formula (Ia) are obtained when 5-difluoromethyl-2-methylsulphonyl-1,3,4-thiadiazole of the formula (II)

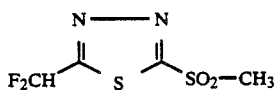

is reacted with hydroxyacetamides of the general formula (III)

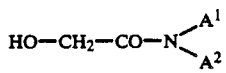

in which A¹ and A² have the abovementioned meanings, if appropriate in the presence of a diluent and if appropriate in the presence of an acid acceptor.

Preferred novel difluoromethyl-thiadizolyl-oxyacetamides of the formula (Ia) are those in which
A¹ stands for isopropyl and
A² stands for phenyl which is optionally substituted by fluorine, chlorine, bromine, cyano, nitro, methyl, ethyl, trifluoromethyl, methoxy and/or ethoxy.

If 5-difluoromethyl-2-methylsulphonyl-1,3,4-thiadoazole and N-isopropyl-hydroxyacetamide are used as starting substances, the process for the preparation of the novel compounds of the formula (Ia) can be outlined by the following equation:

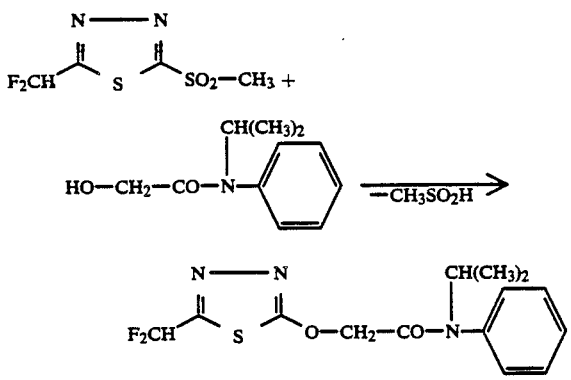

5-Difluoromethyl-2-methylsulphonyl-1,3,4-thiadiazole of the formula (II), which is to be used as the starting substance, was hitherto unknown from the literature and is the subject of the present invention.

The novel compound of the formula (II) is obtained when 5-difluoromethyl-2-methylthio-1,3,4-thiadiazole of the formula (IV)

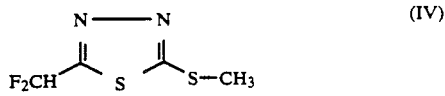

is reacted with an oxidizing agent, such as, for example, hydrogen peroxide, if appropriate in the presence of a catalyst, such as, for example, sodium tungstate, and if appropriate in the presence of diluents, such as, for example, water, formic acid and/or acetic acid, at temperatures between 0° C. and 110° C.

5-Difluoromethyl-2-methylthio-1,3,4-thiadiazole of the formula (IV), which is required as intermediate, was likewise hitherto unknown from the literature and is the subject of the present invention.

The novel compound of the formula (IV) is obtained when diflucroacetic acid is reacted with methyl dithiocarbazate in the presence of an acid acceptor, such as, for example, potassium carbonate, and if appropriate in the presence of a diluent, such as, for example, toluene, at temperatures between 0° C. and 100° C.

Formula (III) provides a general definition of the hydroxyacetamides also to be used as starting substances. In formula (III),
A¹ preferably stands for isopropyl and
A² preferably stands for phenyl which is optionally substituted by fluorine, chlorine, bromine, cyano, nitro, methyl, ethyl, trifluoromethyl, methoxy and/or ethoxy.

Examples of the starting substances of the formula (III) which may be mentioned are:
N-Isopropyl-hydroxyacetanilide, 2'-fluoro-, 3'-fluoro-, 4'-fluoro-, 3',4'-difluoro-, 2',4'-difluoro-, 2',6'-difluoro-, 2'-chloro-, 3'-chloro-, 4'-chloro-, 2',4'-dichloro-, 3',4'-dichloro-, 2',6'-dichloro-, 2',5'-dichloro-, 3',5'-dichloro-, 2'-chloro-6'-fluoro-, 3'-bromo-, 4'-bromo-, 3'-cyano-, 4'-cyano-, 3'-nitro-, 4'-nitro-, 2'-methyl-, 3'-methyl-, 4'-methyl-, 2',3'-dimethyl-, 2',4'-dimethyl-, 2',5'-dimethyl-, 3',4'-dimethyl-, 2'-methyl-5'-nitro-, 2'-chloro-5'-methyl-, 5'-chloro-2'-methyl-, 2'-chloro-6'-methyl-, 3'-ethyl-, 4'-ethyl-, 3'-trifluoromethyl-, 4'-trifluoromethyl-, 2'-trifluoromethyl-, 2'-methoxy-, 3'-methoxy-, 3'-ethoxy- and 4'-ethoxy-N-isopropyl-hydroxyacetanilide.

The hydroxyacetamides of the formula (III) have been disclosed and/or can be prepared by processes known per se (cf., EP-A 37,526, U.S. Pat. Nos. 4,509,971, 4,645,525, 4,334,073).

The process according to the invention for the preparation of the novel compounds of the formula (Ia) is preferably carried out using diluents. Suitable diluents in this process are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone, hexamethylphosphoric triamide and water.

Acid acceptors which can be employed in the process according to the invention are all acid-binding agents which can customarily be employed for reactions of this type. Alkali metal hydroxides, such as, for example, sodium hydroxide and potassium hydroxide, alkali earth metal hydroxides, such as, for example, calcium hydroxide, alkali metal carbonates and alkali metal alkoxides, such as sodium carbonate, potassium carbonate, sodium tert-butoxide and potassium tert-butoxide, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO) are preferably suitable.

In the process according to the invention, the reaction temperatures can be varied within a relatively wide range. In general, the process is carried out at temperatures between $-50°$ C. and $+110°$ C., preferably at temperatures between $-20°$ C. and $+100°$ C.

The process according to the invention is generally carried out at atmospheric pressure. However, it is also possible to carry out the process under increased or reduced pressure.

For carrying out the process according to the invention, the starting substances required in each case are generally employed in approximately equimolar amounts. However, it is also possible to employ one of the two reactants used in each case in relatively large excess. The reactions are generally carried out in a suitable diluent in the presence of an acid acceptor, and the reaction mixture is stirred at the particular temperature required for several hours. In the process according to the invention, working up is carried out in each base by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for selectively combating monocotyledon weeds in monocotyledon and dicotyledon crops, such as, for example, in barley, wheat, corn, rice, soy beans, cotton, beets, potatoes and oilseed rape, in particular in soy beans and cotton, mainly using the pre-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylarl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or lattices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (META-MITRON) for combating weeds in sugar beets, and 4-amino-6-(1,1-dimethylethyl)-3-methylthio-1,2,4-triazin-5(4H)-one (METRIBUZIN) for combating weeds in soy beans; furthermore also 5-amino-4-chloro-2-phenyl-2,3-dihydro- 3-oxy-pyridazine (CHLORIDAZON); ethyl 2-{[(4-chloro-6-methoxy-2-pyrimidinyl)-aminocarbonyl]-aminosulphonyl}-benzoate (CHLORIMURON); 2-[(2-chlorophenyl)-methyl]-4,4-dimethylisoxazolidin-3-one (DIMETHAZONE); N,N-dimethyl-N'-(3-trifluoromethylphenyl)-urea (FLUOMETURON); 1-methyl-3-phenyl-5-(3-trifluoromethylphenyl)-4-pyridone (FLURIDONE); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethyl-pyridine-3-carboxylic acid (IMAZETHAPYR); N-methyl-2-(1,3-benzothiazol-2-yl-oxy)-acetanilide (MEFENACET); 1-(3-trifluoromethyl-phenyl)-4-methylamino-5-chloro-6-pyridazone (NORFLURAZON); N-(1-ethylpropyl)-3,4-dimethyl-2,6-dinitroaniline (PENDIMETHALIN); methyl 3-[[[[(4-methoxy-6-methyl-1,3,5-triazin-2-yl)-amino]-carbonyl]-amino]-sulphonyl]-thiophene-2-carboxylate (THIAMETURON) and 2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

USE EXAMPLES

In the following Use Examples, the compound of the formula below is employed as comparison substance:

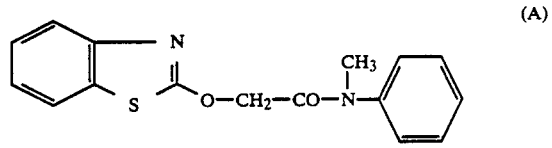

(A)

N-Methyl-2-(benzothiazol-2-yl-oxy)-acetanilide (disclosed in EP-A 5,501 and U.S. Pat. No. 4,509,971).

Example A

Pre-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example the compounds of Examples (2), (3), (4), (5), (6), (8), (10), (12), (13), (14), (15), (16), (17), (18), (19), (20), (21) and (22) from Table 1 are clearly superior compared with the prior art.

PREPARATION EXAMPLES

Example 1

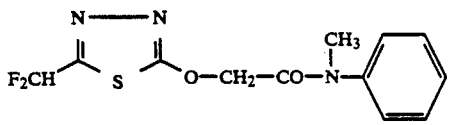

A solution of 1.44 g (0.036 mol) of sodium hydroxide in 6 ml of water is added dropwise to a stirred mixture, cooled at −20° C., of 6.4 g (0.03 mol) of 5-difluoromethyl-2-methylsulphonyl-1,3,4-thiadiazole, 4.9 g (0.03 mol) of N-methyl-hydroxyacetanilide and 50 ml of acetone, and the reaction mixture is stirred for 12 hours while being cooled using an ice/salt mixture. The reaction mixture is then acidified using acetic acid and evaporated under a waterpump vacuum. The residue is washed with toluene/water, dried using sodium sulphate and filtered. The solvent is carefully removed from the filtrate by distillation under a waterpump vaccum.

8.8 g (98% of theory) of N-methyl-2-(5-difluoromethyl-1,3,4-thiadiazol-2-yl-oxy)-acetanilide are obtained as a crystalline residue of melting point 67° C.

Example 2

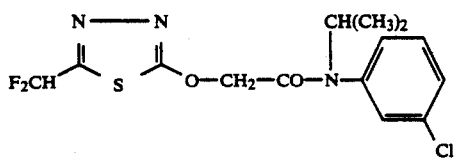

A solution of 1.44 g (0.036 mol) of sodium hydroxide in 6 ml of water is added dropwise to a stirred mixture, cooled at −20° C., of 6.4 g (0.03 mol) of 5-difluoromethyl-2-methylsulphonyl-1,3,4-thiadiazole, 7.2 g (0.03 mol) of N-(3-chloro-phenyl)-N-isopropylhydroxyacetamide and 50 ml of acetone, and the reaction mixture is stirred for 15 hours while being cooled using an ice/salt mixture. The reaction mixture is then acidified using acetic acid and evaporated under a waterpump vaccum. The product, which is obtained crystalline upon subsequent dilution with water, is isolated by filtering off with suction.

11 g (~100% of theory) of N-(3-chloro-phenyl)-N-isopropyl-2-(5-difluoromethyl-1,3,4-thiadiazol-2-yl-oxy)-acetamide of melting point 98° C. are obtained.

Analogously to Examples 1 and 2 and following the general instructions for the preparation process according to the invention, for example the other compounds of the formula (I) or (Ia) which are listed in Table 1 (above) can also be prepared.

Starting Compound of the Formula (II)

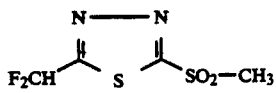 (II)

420 ml of a 35% strength aqueous hydrogen peroxide solution are added dropwise to a stirred mixture, heated at 50° C., of 198 g (1.28 mol) of 5-difluoromethyl-2-methylthio-1,3,4-thiadiazole, 390 ml of formic acid and 0.8 g of sodium tungstate, during which process the temperature rises briefly to 95° C. The product which is obtained crystalline in this process is then isolated by filtering off with suction.

250 g (91% of theory) of 5-difluoromethyl-2-methylsulphonyl-1,3,4-thiadiazole of melting point 59° C. are obtained.

Starting Compound of the Formula (IV)

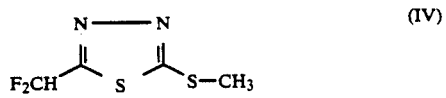 (IV)

131 g (1.29 mol) of difluoroacetic acid are added dropwise at 20° C. to a stirred mixture of 89 g (0.65 mol) of potassium carbonate and 130 ml of water. After the addition of 300 ml of toluene, the water is removed by azeotropic distillation in a water separator. A further 700 ml of toluene and 156 g (1.29 mol) of methyl dithiocarbazate are added to the remaining organic phase. 404 g (1.61 mol) of phosphorus oxychloride are then added dropwise at 50° C. to 60° C., the mixture is stirred for 2 hours and then poured into ice water. The organic phase is separated off, washed with water, dried using sodium sulphate and filtered. The solvent is removed from the filtrate by distillation under a water-pump vacuum.

190 g (96% of theory) of 5-difluoromethyl-2-methylthio-1,3,4-thiadiazole are obtained as amorphous residue which crystallizes gradually. Melting point: 23° C.

It will be appreciated that the instant specification and claims are set forth by way of illustration and not limitation, and that various modifications and changes may be made without departing from the spirit and scope of the present invention.

What is claimed is:

1. A difluoromethyl-thiadiazolyl-oxyacetamide of the formula

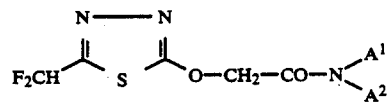

in which
$A^1$ stands for $C_2$-$C_4$-alkyl and
$A^2$ stands for phenyl which is optionally substituted by fluorine, chlorine, bromine, cyano, nitro, methyl, ethyl, trifluoromethyl, methoxy and/or ethoxy.

2. A difluoromethyl-thiadiazolyl-oxyacetamide according to claim 1, in which
$A^1$ stands for isopropyl.

3. A compound according to claim 1, wherein such compound is N-(3-chloro-phenyl)-N-isopropyl-2-(5-difluoromethyl-1,3,4-thiadiazol-2-yl-oxy)-acetamide of the formula

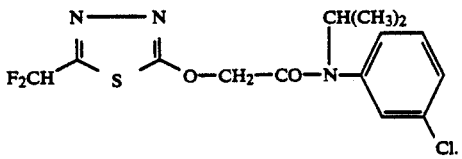

4. A compound according to claim 1, wherein such compound is N-(4-chloro-phenyl)-N-isopropyl-2-(5-difluoromethyl-1,3,4-thiadiazol-2-yl-oxy)-acetamide of the formula

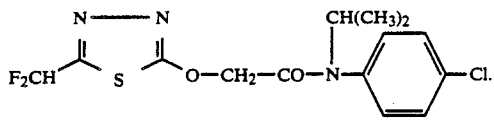

5. A compound according to claim 1, wherein such compound is N-(4-fluoro-phenyl)-N-isopropyl-2-(5-difluoromethyl-1,3,4-thiadiazol-2-yl-oxy)-acetamide of the formula

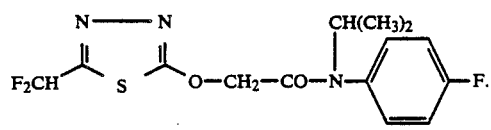

6. A herbicidal composition comprising a herbicidally effective amount of a compound according to claim 1 and a diluent.

7. A process for selectively combating weeds in crops, comprising applying to a locus in which such crops are growing or are to be grown a herbicidally effective amount of a difluoromethyl-thiadiazolyl-oxy-acetamide according to claim 1.

8. The method according to claim 7, wherein such compound is
N-(3-chloro-phenyl)-N-isopropyl-2-(5-difluoromethyl-1,3,4-thiadiazol-2-yl-oxy)-acetamide,
N-(4-chloro-phenyl)-N-isopropyl-2-(5-difluoromethyl-1,3,4-thiadiazol-2-yl-oxy)-acetamide or
N-(4-fluoro-phenyl)-N-isopropyl-2-(5-difluoromethyl-1,3,4-thiadiazol-2-yl-oxy-acetamide.

9. The method according to claim 7, wherein such crop is soy beans, cotton or corn.

* * * * *